(12) United States Patent
Beschorner et al.

(10) Patent No.: US 10,459,462 B2
(45) Date of Patent: Oct. 29, 2019

(54) SENSOR FUSION FEEDBACK FOR CONTROLLING FLUID PRESSURES IN A MACHINE

(71) Applicant: CATERPILLAR INC., Peoria, IL (US)

(72) Inventors: Matthew James Beschorner, Plainfield, IL (US); Justin Douglas Speichinger, Edwards, IL (US); Shogo Tada, Peoria, IL (US); Rustin Glenn Metzger, Congerville, IL (US)

(73) Assignee: Caterpillar Inc., Peoria, IL (US)

( * ) Notice: Subject to any disclaimer, the term of this patent is extended or adjusted under 35 U.S.C. 154(b) by 302 days.

(21) Appl. No.: 15/629,172

(22) Filed: Jun. 21, 2017

(65) Prior Publication Data

US 2018/0373275 A1    Dec. 27, 2018

(51) Int. Cl.
| | |
|---|---|
| G05D 16/08 | (2006.01) |
| E02F 9/26 | (2006.01) |
| G01N 33/28 | (2006.01) |
| G01S 17/89 | (2006.01) |
| G01S 17/02 | (2006.01) |
| G01C 21/16 | (2006.01) |
| E02F 9/22 | (2006.01) |

(52) U.S. Cl.
CPC .......... *G05D 16/08* (2013.01); *E02F 9/2235* (2013.01); *E02F 9/264* (2013.01); *E02F 9/265* (2013.01); *G01C 21/165* (2013.01); *G01N 33/28* (2013.01); *G01S 17/023* (2013.01); *G01S 17/89* (2013.01); *E02F 9/2246* (2013.01)

(58) Field of Classification Search
CPC ........ G05D 16/08; E02F 9/265; E02F 9/2235; E02F 9/264; E02F 9/2246; G01C 21/165; G01N 33/28; G01S 17/89; G01S 17/023
See application file for complete search history.

(56) References Cited

U.S. PATENT DOCUMENTS

| | | | |
|---|---|---|---|
| 8,065,060 B2 * | 11/2011 | Danko | B25J 9/1628 700/11 |
| 2017/0107700 A1 * | 4/2017 | Faivre | E02F 9/2029 |
| 2018/0224280 A1 * | 8/2018 | Alam | G01C 19/5776 |

* cited by examiner

*Primary Examiner* — Michael J Zanelli
(74) *Attorney, Agent, or Firm* — Finnegan, Henderson, Farabow, Garrett & Dunner, LLP

(57) ABSTRACT

A method of using sensor feedback for controlling fluid pressures in a machine includes receiving signals from each of a plurality of Inertial Measurement Units (IMU's) mounted on different components of the machine, receiving a signal from at least one non-IMU sensor, fusing the signals received from the IMU's with each other and with a signal from the at least one non-IMU sensor, determining best estimates of current output joint angles for each of the plurality of components of the machine with reference to a machine reference frame, solving a kinematic equation using the best estimates of current output joint angles for the components of the machine and structural design information characterizing the machine, and applying a determination from the solution of the kinematic equation in an implementation of a controlled adjustment to a fluid pressure supplied to a fluid actuation cylinder.

20 Claims, 5 Drawing Sheets

SENSOR FUSION FEEDBACK FOR CONTROLLING FLUID PRESSURES IN A MACHINE

TECHNICAL FIELD

The present disclosure relates generally to controlling fluid pressures in a machine and, more particularly, to using sensor fusion feedback for controlling fluid pressures in a machine.

BACKGROUND

Machines such as, for example, dozers, motor graders, wheel loaders, wheel tractor scrapers, and other types of heavy equipment are used to perform a variety of tasks. Effective control of the machines requires accurate and responsive sensor reading to perform calculations providing information in near real time to the machine control or operator. Autonomously and semi-autonomously controlled machines are capable of operating with little or no human input by relying on information received from various machine systems. For example, based on machine movement input, terrain input, and/or machine operational input, a machine can be controlled to remotely and/or automatically complete a programmed task. By receiving appropriate feedback from each of the different machine systems and sensors during performance of the task, continuous adjustments to machine operation can be made that help to ensure precision and safety in completion of the task. In order to do so, however, the information provided by the different machine systems and sensors should be accurate and reliable. The position, velocity, and distance traveled by the machine, and positions, movements, and orientations of different parts or components of the machine are parameters whose accuracy may be important for control of the machine and its operations.

Conventional machines typically utilize a navigation or positioning system to determine various operating parameters such as position, velocity, pitch rate, yaw rate, and roll rate for the machine. The position and orientation of the machine is referred to as the "pose" of the machine. The machine "state" includes the pose of the machine as well as various additional operating parameters that can be used to model the kinematics and dynamics of the machine, such as parameters characterizing the various links, joints, tools, hydraulics, and power systems of the machine. Some conventional machines utilize a combination of one or more of Global Navigation Satellite System (GNSS) data, a Distance Measurement Indicator (DMI) or odometer measurement data, Inertial Measurement Unit (IMU) data, etc. to determine these parameters. Some machines utilize RADAR sensors, SONAR sensors, LIDAR sensors, IR and non-IR cameras, and other similar sensors to help guide the machines safely and efficiently along different kinds of terrain. Conventional machines have attempted to fuse these different types of data to determine the position of a land-based vehicle.

An exemplary system that may be utilized to determine the position of a machine is disclosed in U.S. Patent Application Publication No. 2008/0033645 ("the '645 publication") to Levinson et al. that published on Feb. 7, 2008. The system of the '645 publication utilizes location data from sensors such as Global Positioning System (GPS), as well as scene data from a LIDAR (light detection and ranging) device to determine a location or position of the machine. Specifically, the data is used to create a high-resolution map of the terrain and the position of the machine is localized with respect to the map.

Although the system of the '645 publication may be useful in determining the overall position of the machine, the system may not provide accurate estimates for the position of the machine or components of the machine while dead-reckoning (i.e., during periods of time when GPS signals are unavailable). Moreover, the system of the '645 publication may not provide accurate position information when GPS signals are unreliable or erroneous due to multipath errors, position jumps, etc. because the system of the '645 publication does not check for the accuracy of the GPS signal.

The system and method for using sensor fusion feedback for controlling fluid pressures in a machine according to the present disclosure is directed toward solving one or more of the problems set forth above and/or other problems of the prior art.

SUMMARY

In one aspect, the present disclosure is directed to a method of using sensor fusion feedback in the control of fluid pressures in a machine. The method includes receiving, with at least one processor, from each of a plurality of Inertial Measurement Units (IMU's) mounted on different components of the machine, a time series of signals indicative of acceleration and angular rate of motion measurements for each of the components of the machine on which one or more of the plurality of IMU's are mounted. The method also includes receiving, with at least one processor, from at least one non-IMU sensor, a signal indicative of at least one of position, velocity, or acceleration of at least one of the machine components; position, velocity, or acceleration of any potential obstacles or other features at a job site where the machine is operating; a fluid pressure; an engine speed; a fluid relief pressure; a maximum pump output pressure; or an operator input. The method further includes, for each one of the IMU's on a separate component of the machine, fusing the signals received from the IMU with a separate Kalman filter module of the at least one processor, the fusing of the signals from each one of the plurality of IMU's including combining an acceleration measurement and an angular rate of motion measurement from the IMU to estimate an output joint angle for the component of the machine on which the IMU is mounted during a timestep of a series of timesteps. The method still further includes generating an a priori estimate of the output joint angle for the component in a subsequent timestep based on an estimate of the output joint angle from a previous timestep, and combining the a priori estimate of the output joint angle with an estimate of the accuracy of the a priori estimate and a current measurement value received from the IMU to produce a refined a posteriori estimate of the output joint angle. The method may also include fusing the refined a posteriori estimates of the output joint angles for a plurality of the components of the machine with each other, with a signal from the at least one non-IMU sensor, and in reference to a machine reference frame to determine best estimates of current output joint angles for each of the plurality of components of the machine with reference to the machine reference frame. The method may also include solving a kinematic equation using the best estimates of current output joint angles for the components of the machine and structural design information characterizing the machine, determining from the solution of the kinematic equation whether a higher fluid pressure to a fluid actuation cylinder connected between two of the machine components is required to avoid stalling of one of the two machine components relative to the other of the two machine components under load after each successive timestep of the series of timesteps, determining from the solution of the kinematic equation whether an adjustment to a pressure cut off for a fluid pump on the machine is required for an operation, and applying a determination from the solution of the kinematic equation in an implementation of a controlled adjustment to a fluid pressure supplied to the fluid actuation cylinder.

In another aspect, the present disclosure is directed to a system for using sensor fusion feedback in the control of fluid pressures in a machine. The system includes a plurality of Inertial Measurement Units (IMU's) mounted on separate components of the machine, the IMU's each being configured to generate a time series of signals indicative of acceleration and angular rate of motion measurements for the component of the machine on which the IMU is mounted, at least one non-IMU sensor configured to generate a signal indicative of at least one of position, velocity, or acceleration of at least one of the machine components, position, velocity, or acceleration of any potential obstacles or other features at a job site where the machine is operating, a fluid pressure, an engine speed, a fluid relief pressure, a maximum pump output pressure, or an operator input, and at least one processor in communication with each of the IMU's and the at least one non-IMU sensor. Each of the at least one processor may be configured to fuse the signals received from the IMU with a separate Kalman filter module of the at least one processor, the fusing of the signals from each one of the plurality of IMU's including combining an acceleration measurement and an angular rate of motion measurement from the IMU to estimate an output joint angle for the component of the machine on which the IMU is mounted during a timestep of a series of timesteps, generating an a priori estimate of the output joint angle for the component in a subsequent timestep based on an estimate of the output joint angle from a previous timestep, and combining the a priori estimate of the output joint angle with an estimate of the accuracy of the a priori estimate and a current measurement value received from the IMU to produce a refined a posteriori estimate of the output joint angle. Each processor may also be configured to fuse the refined a posteriori estimates of the output joint angles for a plurality of the components of the machine with each other, with a signal from the at least one non-IMU sensor, and in reference to a machine reference frame to determine best estimates of current output joint angles for each of the plurality of components of the machine with reference to the machine reference frame. Each processor may be further configured to solve a kinematic equation using the best estimates of current output joint angles for the components of the machine and structural design information characterizing the machine, and determine from the solution of the kinematic equation whether a higher fluid pressure to a fluid actuation cylinder connected between two of the machine components is required to avoid stalling of one of the two machine components relative to the other of the two machine components under load after each successive timestep of the series of timesteps. Each processor may be still further configured to determine from the solution of the kinematic equation whether an adjustment to a pressure cut off for a fluid pump on the machine is required for an operation, and apply a determination from the solution of the kinematic equation in an implementation of a controlled adjustment to a fluid pressure supplied to the fluid actuation cylinder.

In yet another aspect, the present disclosure is directed to a non-transitory computer-readable storage device storing instruction for enabling a processor to execute a method of using sensor fusion feedback in the control of fluid pressures in a machine. The method may include receiving, with the processor, from each of a plurality of Inertial Measurement Units (IMU's) mounted on different components of the machine, a time series of signals indicative of acceleration and angular rate of motion measurements for each of the components of the machine on which one or more of the plurality of IMU's are mounted. The method may also include receiving, with the processor, from at least one non-IMU sensor, a signal indicative of at least one of position, velocity, or acceleration of at least one of the machine components, position, velocity, or acceleration of any potential obstacles or other features at a job site where the machine is operating, a fluid pressure, an engine speed, a fluid relief pressure, a maximum pump output pressure, or an operator input. The method may still further include, for each one of the IMU's on a separate component of the machine, fusing the signals received from the IMU with a separate Kalman filter module of the processor, the fusing of the signals from each one of the plurality of IMU's including combining an acceleration measurement and an angular rate of motion measurement from the IMU to estimate an output joint angle for the component of the machine on which the IMU is mounted during a timestep of a series of timesteps, generating an a priori estimate of the output joint angle for the component in a subsequent timestep based on an estimate of the output joint angle from a previous timestep, and combining the a priori estimate of the output joint angle with an estimate of the accuracy of the a priori estimate and a current measurement value received from the IMU to produce a refined a posteriori estimate of the output joint angle. The method may also include fusing the refined a posteriori estimates of the output joint angles for a plurality of the components of the machine with each other, with a signal from the at least one non-IMU sensor, and in reference to a machine reference frame to determine best estimates of current output joint angles for each of the plurality of components of the machine with reference to the machine reference frame. The method may include solving a kinematic equation using the best estimates of current output joint angles for the components of the machine and structural design information characterizing the machine, determining from the solution of the kinematic equation whether a higher fluid pressure to a fluid actuation cylinder connected between two of the machine components is required to avoid stalling of one of the two machine components relative to the other of the two machine components under load after each successive timestep of the series of timesteps, and determining from the solution of the kinematic equation whether an adjustment to a pressure cut off for a fluid pump on the machine is required for an operation. The method may still further include applying a determination from the solution of the kinematic equation in an implementation of a controlled adjustment to a fluid pressure supplied to the fluid actuation cylinder.

DETAILED DESCRIPTION

Figure 1:
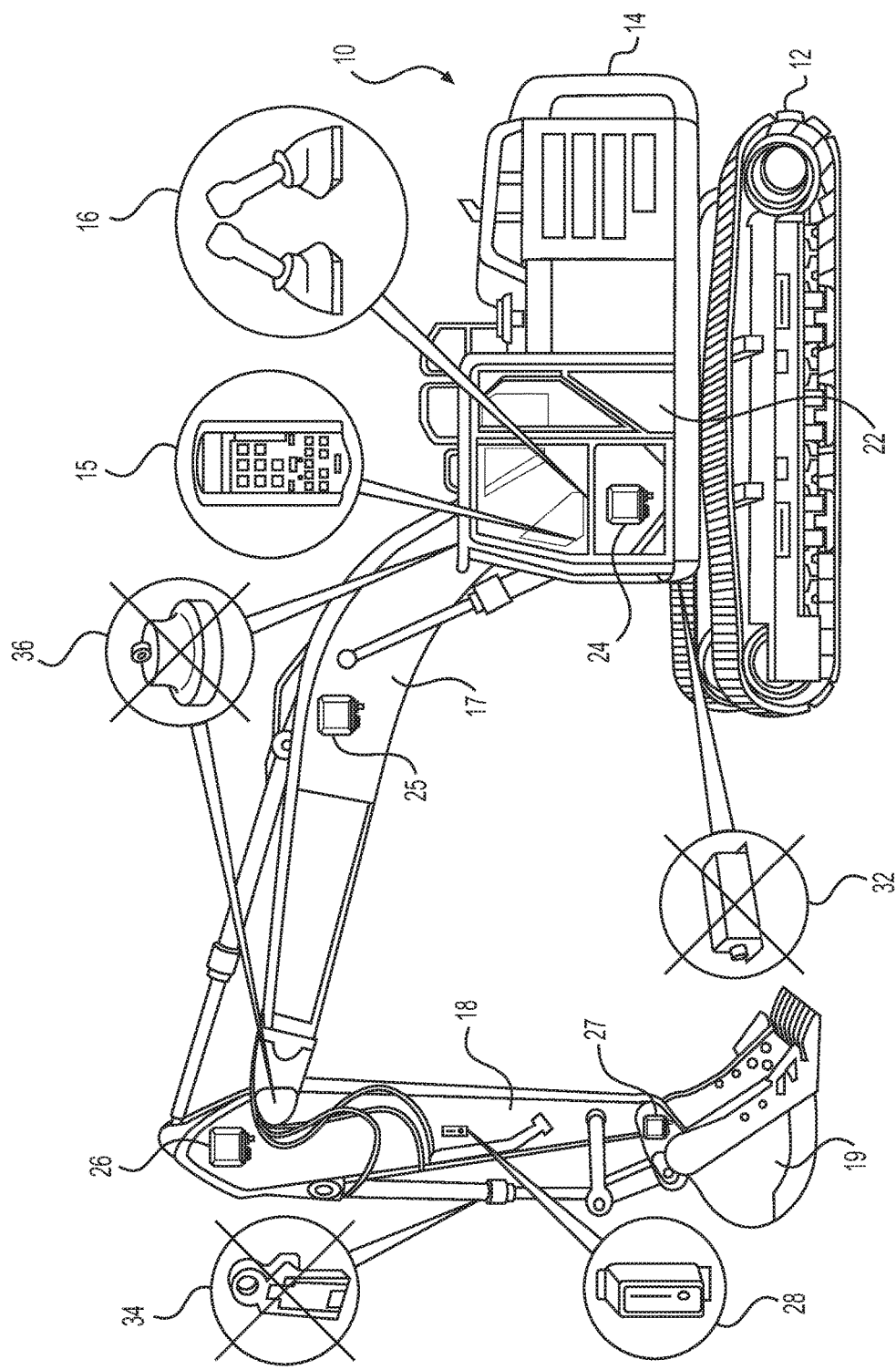
FIG. 1 is a pictorial illustration of an exemplary disclosed machine, which may be operated using a system and method for determining the real time state of the machine according to exemplary embodiments of this disclosure.

FIG. 1 illustrates a machine 10 including a plurality of Inertial Measurement Units (IMU's) 24, 25, 26, and 27 applied at different positions on components or portions of the machine 10, such as on the machine body 14, the boom 17, the stick 18, and the bucket (or other tool) 19. In a machine state control system according to various exemplary embodiments of this disclosure, the IMU's mounted on different components and/or portions of the machine 10 may replace or supplement conventional sensors such as pitch and roll sensors 32, cylinder position sensors 34, and rotary position sensors 36. Each IMU may include one or more accelerometers, one or more gyroscopes, and in some cases a magnetometer for providing signals indicative of direction relative to earth's magnetic poles. The accelerometers and gyroscopes of each IMU provide signals that can be used to discern the position and orientation of the IMU relative to a body frame of reference, and hence of the machine component to which the IMU is attached. The IMU's may provide a lower cost and more reliable alternative to traditional sensors such as position sensing cylinders and rotary position sensors, and may also be more easily retrofittable to existing machines by simply welding the IMU's on different external portions of the machine without requiring disassembly of the machine or of components of the machine. A machine electronic control module (ECM) configured to send control signals to the various systems and subsystems of the machine may be reprogrammed and configured to receive signals from the retrofitted IMU's, with the signals being processed and converted to real time inputs used by the ECM to modify control signals based on the inputs.

Various non-IMU sensors 230 (see FIG. 2) may be added or removed depending on the particular machine application and configuration. The non-IMU sensors may include various perception sensors included as part of a vision system, position and/or velocity sensors, such as an upper structure position/velocity sensor 22, a laser catcher sensor 28 configured to provide a signal indicative of position as measured by a laser, a cylinder position sensor 34, hydraulic system sensors, electrical system sensors, braking system sensors, fuel system sensors, and other sensors providing real time inputs to the ECM for use in monitoring the status of and controlling the operation of the systems and subsystems of the machine.

The machine 10 may be configured to perform some type of operation associated with an industry such as mining, construction, farming, transportation, power generation, or any other industry known in the art. For example, the machine 10 may be an earth moving machine such as a haul truck, a dozer, a loader, a backhoe, an excavator, a motor grader, a wheel tractor scraper or any other earth moving machine. The machine 10 may generally include track assemblies or other traction devices 12 (i.e., ground engagement devices) that are mounted on a car body (in between the track assemblies), which supports a rotating frame on which the machine body 14 forming an upper structure is mounted. The rotating frame and machine body 14 may support an operator station or cab, an integrated display 15 mounted within the cab, operator controls 16 (such as integrated joysticks mounted within the cab), and one or more engines and drive trains that drive the traction devices 12 to propel the machine 10. The boom 17 may be pivotally mounted at a proximal end to the machine body 14, and articulated relative to the machine body 14 by one or more fluid actuation cylinders (e.g., hydraulic or pneumatic cylinders), electric motors, or other electro-mechanical components. The stick 18 may be pivotally mounted at a distal end of the boom 17 and articulated relative to the boom by one or more fluid actuation cylinders, electric motors, or other electro-mechanical components. The tool 19, such as a bucket, may be mounted at a distal end of the stick 18, optionally articulated relative to the stick 18 by one or more fluid actuation cylinders, electric motors, or other electro-mechanical components, and provided with ground engagement tools or other attachments for performing various tasks.

Figure 2:
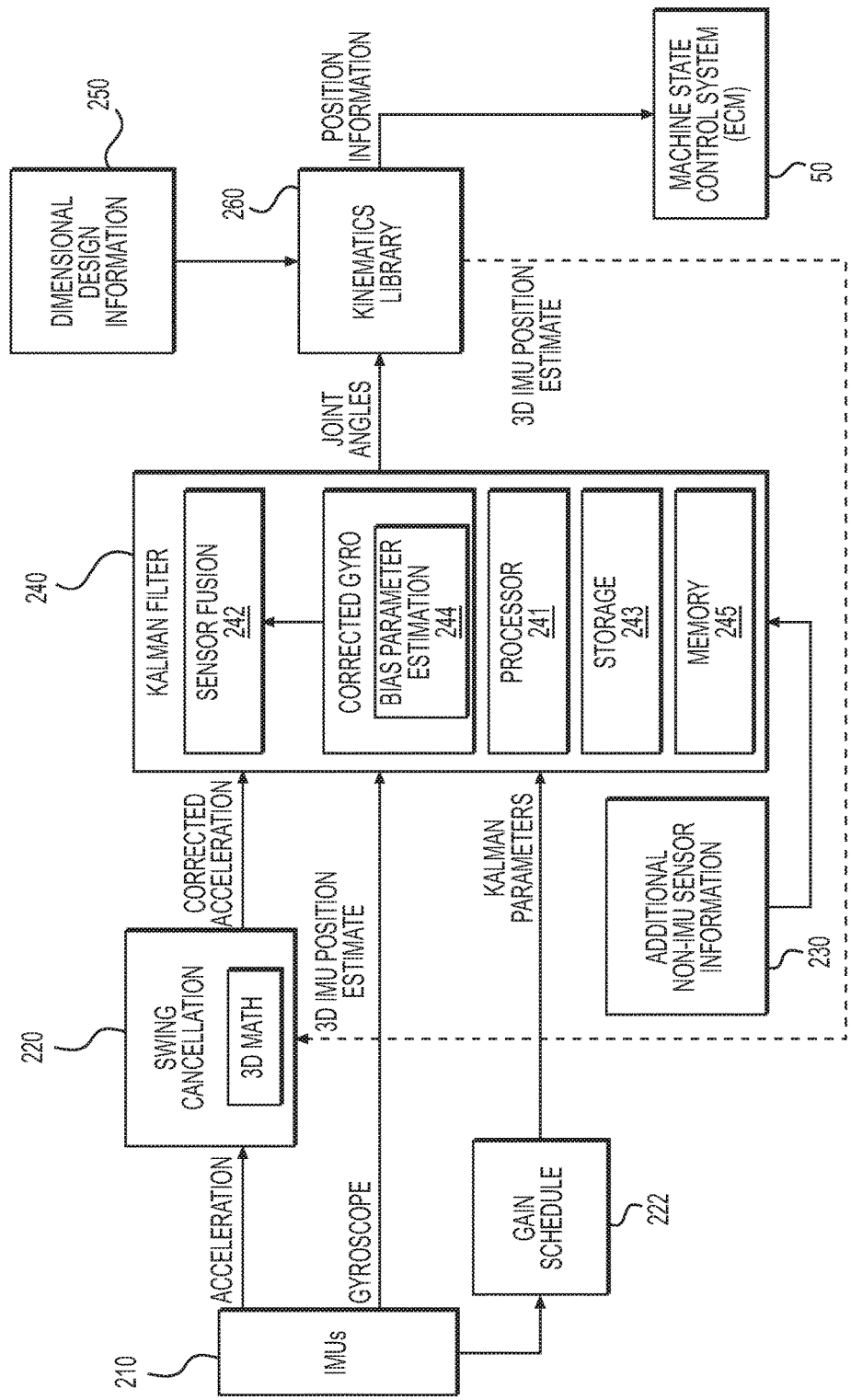
FIG. 2 is a diagrammatic illustration of an exemplary disclosed sensor fusion system for determining the state of the machine of FIG. 1.

FIG. 2 is a block diagram of an exemplary embodiment of a sensor fusion system according to the present disclosure. The sensor fusion system may be configured to provide accurate, real time outputs to a machine state control system 50 configured for controlling various operational aspects of the machine 10. The machine state control system 50 may be associated with or an integral part of the machine ECM. The sensor fusion system may be configured to receive signals from a plurality of IMU's 210 and additional non-IMU sensors 230, as well as signals indicative of various operator commands, such as signals generated by an operator's movement of a joystick or other input device or operator control 16. "Sensor fusion" is the combining of the sensory data or data derived from disparate sources such that the resulting information has less uncertainty than would be possible when the sources were used individually. The sensor fusion system may also be configured to receive information on the dimensional design of the particular machine with which the sensor fusion system is associated from a dimensional design information database 250. The particular dimensional design information received from the design information database 250 for a particular machine may be used by a processor 241 associated with the sensor fusion system and configured for deriving the kinematics and dynamics of the machine 10 in conjunction with a kinematics library module 260 and/or through the empirical derivation of the kinematics and dynamics using physics-based equations and algorithms. The various sensors and processors may be connected to each other via any suitable architecture, including any combination of wired and/or wireless networks. Additionally, such networks may be integrated into any local area network (LAN), wide area network (WAN), and/or the Internet.

The IMU's 210 may be applied to the machine in multiple different positions and orientations, including on different portions of the machine body 14, the boom 17, the stick 18, and the work tool (e.g., the bucket) 19. The IMU's may be retrofitted at multiple positions and orientations along each of the portions of the machine, and may be added and removed depending on a particular machine application and configuration. Raw data received from each IMU may be processed through a Kalman filter, as will be described in more detail below. In some implementations the Kalman filter for each IMU sensor may be included as part of the IMU, and in other implementations the Kalman filter may be part of a separate sensor fusion module provided as part of a separate sensor fusion system.

Gyroscopes of each IMU sense orientation through angular velocity changes, while accelerometers of each IMU sense changes in direction with respect to gravity. The gyroscope measurements have a tendency to drift over time because they only sense changes and have no fixed frame of reference. The addition of accelerometer data allows bias in the gyroscope data to be minimized and better estimated to reduce propagating error and improve orientation readings. The accelerometers may provide data that is more accurate in static calculations, when the system is closer to a fixed reference point, while the gyroscopes are better at detecting orientation when the system is already in motion. Signals indicative of linear acceleration and angular rate of motion received from the accelerometers and gyroscopes of the IMU's associated with each of the different portions and/or components of the machine may be combined by the Kalman filter(s) to more accurately predict the output angle, velocity, and acceleration of each of the separate components of the machine.

The Kalman filter associated with each IMU mounted on a separate machine component takes measured values and finds estimates of future values by varying an averaging factor to optimize the weight assigned to estimated or predicted values as compared to the weight assigned to actual measured values, thereby converging on the best estimates of the true values for output joint angles, velocity, and acceleration for each component of the machine. The averaging factor is weighed by a measure of predicted uncertainty, sometimes called the covariance, to pick a value somewhere between the predicted and measured values. The Kalman filter estimates a machine state by using a form of feedback control in a recursive and iterative process, with each iteration including a time update or "predict" phase, and a measurement or "correct phase". During each iteration performed by the Kalman filter, a "gain" or weighting is determined by comparing an error in the estimate for a measured value and an error in the actual measurement of the value. The Kalman gain is equal to the ratio between the error in the estimate and the sum of the error in the estimate and the error in the actual measurement. A current estimate for the value is then calculated from the previous estimate and a new measured value. A new error in the estimate of the value is then determined and fed back for use in determining the gain to be applied in the next iteration. The combined or fused information provided by the Kalman filter may provide accurate, real time information on pitch rate, yaw rate, roll rate, boom angle, stick angle, and other angles depending on linkage configuration and the number of IMU's installed on different portions or components of the machine.

As shown in the exemplary embodiment of FIG. 2, a Kalman filter of a sensor fusion system according to this disclosure may be configured to estimate bias of gyroscope information provided by the IMU's, such as the pitch rate, the yaw rate, and the roll rate of each of the components. Because the linear positions and angular positions of points on each of the components are calculated by twice integrating linear accelerations and angular rates of motion from the IMU's, the calculated information can drift over time, deviating more and more from the actual positions as small errors in the measurements are magnified by the integrations. Therefore, the gyroscope biasing aspect of the Kalman filter increases the accuracy of the joint angles calculated from the information provided by the IMU's. The output joint angles for each of the individual portions or components of the machine may be fused with each other at a machine level in order to account for movement of two or more components relative to the machine while the two or more components remain in a substantially fixed orientation relative to each other. For example, both the IMU sensor 25 on the boom 17 of the machine 10 illustrated in FIG. 1, and the IMU sensor 26 on the stick 18 may indicate a change in output joint angles relative to a global reference frame when the boom 17 moves upwardly, however the actual angle between the boom 17 and the stick 18 may not have changed. Fusing the output joint angles for each of the boom 17 and the stick 18 at a machine level will provide this information so that actual positions of different points on the separate machine components relative to a machine reference frame and a global reference frame can be determined in real time.

As further illustrated in the exemplary embodiment of FIG. 2, the output joint angles that have been fused at the machine level by the Kalman filter 240 may be received by a kinematic library module 260. The kinematics library module 260 may be configured to receive the output joint angles from the Kalman filter(s) 240 and dimensional design information specific to the machine 10 from a dimensional design information database 250, and solve for a frame rotation and position at each component or point of interest on the machine. The frame can have offsets applied to the information derived from the IMU's in order to solve for any particular point on the machine, and all of the updated position information can be provided to a machine state control system 50, which may be associated with or programmed as part of the machine ECM.

In the case of an excavator or other machine where IMU's may be mounted on portions of the machine that are rotated or swung through an arc during operation, the 3 dimensional position information associated with each of the IMU's mounted on those portions of the machine may also be fed back to a swing compensation module 220. The swing compensation module 220 may be configured to correct the acceleration information provided by the IMU's mounted on the rotating or swinging portions of the machine by compensating for centripetal acceleration. This correction of the acceleration information received from the IMU's 210 may be performed before the information is provided to the Kalman filter 240.

The additional non-IMU sensors 230 may include any devices capable of generating signals indicative of parametric values or machine parameters associated with performance of the machine 10. For example, the non-IMU sensors 230 may include sensors configured to produce signals indicative of boom and/or stick swing velocity, boom and/or stick position in global and machine reference frames, and work tool angle. A payload sensor may also be included and configured to provide a signal indicative of a payload of the machine 10. A slip detector may be included and configured to provide a signal indicative of a slip of the machine 100. Additional non-IMU sensors may include devices capable of providing signals indicative of a slope of the ground on which the machine 10 is operating, an outside temperature, tire pressure if the traction device 12 is a wheel, hydraulic or pneumatic pressures in various fluid actuation control devices, electrical voltages, currents, and/or power being supplied to electrical control devices, etc.

The non-IMU sensors 230 may include one or more locating devices capable of providing signals indicative of the machine's location and/or the position of various components of the machine relative to a global or local frame of reference. For example, a locating device could embody a global satellite system device (e.g., a GPS or GNSS device) that receives or determines positional information associated with machine 10, and may provide an independent measurement of the machine's position. The locating device and any other non-IMU sensor 230 may be configured to convey signals indicative of the received or determined positional information, or other information relating to various machine operational parameters to one or more interface devices such as the integrated display 15 in the operator cab for display of real time machine operating characteristics. The signals from the IMU's 210 and non-IMU sensors 230 may be directed to a controller configured to include a Kalman filter 240, and the Kalman filter 240 may be configured for implementation by one or more processors 241 associated with storage 243 and memory 245. The one or more processors 241 of the controller may be configured to implement a Kalman filtering process including sensor fusion performed in a sensor fusion module 242. The Kalman filter 240 may also be configured to perform gyroscope bias estimation in a gyroscope bias estimation module 244 in order to compensate for any drift over time in the readings provided by one or more gyroscopes associated with the IMU's. In some exemplary embodiments, a locating device may receive a GPS signal as the location signal indicative of the location of the machine 10 and provide the received location signal to the processor 241 for further processing. Additionally, the locating device may also provide an uncertainty measure associated with the location signal. However, it will be understood by one of ordinary skill in the art that the disclosed exemplary embodiments could be modified to utilize other indicators of the location of the machine 10, if desired.

The non-IMU sensors 230 may also include one or more perception sensors, which may include any device that is capable of providing scene data describing an environment in the vicinity of the machine 10. A perception sensor may embody a device that detects and ranges objects located 360 degrees around the machine 10. For example, a perception sensor may be embodied by a LIDAR device, a RADAR (radio detection and ranging) device, a SONAR (sound navigation and ranging) device, a camera device, or another device known in the art. In one example, a perception sensor may include an emitter that emits a detection beam, and an associated receiver that receives a reflection of that detection beam. Based on characteristics of the reflected beam, a distance and a direction from an actual sensing location of the perception sensor on the machine 10 to a portion of a sensed physical object may be determined. By utilizing beams in a plurality of directions, the perception sensor may generate a picture of the surroundings of the machine 10. For example, if the perception sensor is embodied by a LIDAR device or another device using multiple laser beams, the perception sensor, such as the laser catcher sensor 28 mounted on the stick 18 of the machine, may generate a cloud of points as the scene data describing an environment in the vicinity of the machine 10. It will be noted that the scene data may be limited to the front side (180 degrees or less) of the machine 10 in some embodiments. In other embodiments, the perception sensor may generate scene data for objects located 360 degrees around the machine 10.

The IMU's 210 may include devices that provide angular rates and acceleration of the machine 10 or, more particularly, of components or portions of the machine on which the IMU's are mounted, such as the machine body 14, the boom 17, the stick 18, and the bucket or other tool 19. For example, the IMU's 210 may include a 6-degree of freedom (6 DOF) IMU. A 6 DOF IMU sensor consists of a 3-axis accelerometer, 3-axis angular rate gyroscopes, and sometimes a 2-axis inclinometer. Each of the IMU's 210 may be retrofitted to an existing machine by welding the IMU to a portion or component of the machine where precise information on the real time position, orientation, and motion of that particular portion or component of the machine is desired. The machine's electronic control module (ECM) or other machine controller(s) may be programmed to receive signals from the IMU's and implement various machine controls based at least in part on the inputs received from the IMU's. In some exemplary implementations of this disclosure, the controls implemented by an ECM in response to the signals received from the IMU's may include actuation of one or more electrical or electro-hydraulic solenoids that are configured to control the opening and closing of one or more valves regulating the supply of pressurized hydraulic or pneumatic fluid to one or more fluid actuation cylinders. The 3-axis angular rate gyroscopes associated with the IMU's may be configured to provide signals indicative of the pitch rate, yaw rate, and roll rate of the machine 100 or of the specific portion of the machine on which the IMU sensor is mounted. The 3-axis accelerometer may be configured to provide signals indicative of the linear acceleration of the machine 10 or portion of the machine on which the IMU sensor is mounted, in the x, y, and z directions.

The Kalman filter module 240 may be associated with one or more of the processor 241, storage 243, and memory 245, included together in a single device and/or provided separately. The processor 241 may include one or more known processing devices, such as a microprocessor from the Pentium™ or Xeon™ family manufactured by Intel™, the Turion™ family manufactured by AMD™, any of various processors manufactured by Sun Microsystems, or any other type of processor. The memory 245 may include one or more storage devices configured to store information used by the Kalman filter 240 to perform certain functions related to disclosed embodiments. The storage 243 may include a volatile or non-volatile, magnetic, semiconductor, tape, optical, removable, nonremovable, or other type of storage device or computer-readable medium or device. The storage 243 may store programs and/or other information, such as information related to processing data received from one or more sensors, as discussed in greater detail below.

In one embodiment, the memory 245 may include one or more position estimation programs or subprograms loaded from the storage 243 or elsewhere that, when executed by the processor 241, perform various procedures, operations, or processes consistent with the disclosed embodiments. For example, the memory 245 may include one or more programs that enable the Kalman filter 240 to, among other things, collect data from an odometer, a locating device, a perception sensor, any one or more of the IMU's 210, and any one or more of the non-IMU sensors 230, and process the data according to disclosed embodiments such as those embodiments discussed with regard to FIG. 5, and estimate the position(s) of the machine 10 and various portions and components of the machine in real time based on the processed data.

In certain exemplary embodiments, position estimation programs may enable the Kalman filter 240 of the processor 241 to process the received signals to estimate the real time positions and orientations of different portions or components of the machine 10. A Kalman filter implements a method that may be used to determine accurate values of measurements observed over time, such as measurements taken in a time series. The Kalman filter's general operation involves two phases, a propagation or "predict" phase and a measurement or "update" phase. In the predict phase, the value estimate from the previous timestep in the time series is used to generate an a priori value estimate. In the update phase, the a priori estimate calculated in the predict phase is combined with an estimate of the accuracy of the a priori estimate (e.g., the variance or the uncertainty), and a current measurement value to produce a refined a posteriori estimate. The Kalman filter is a multiple-input, multiple output digital filter that can optimally estimate, in real time, the states of a system based on its noisy outputs. These states are all the variables needed to completely describe the system behavior as a function of time (such as position, velocity, voltage levels, and so forth). The multiple noisy outputs can be thought of as a multidimensional signal plus noise, with the system states being the desired unknown signals indicative of the true values for each of the variables. The Kalman filter 240 can be configured to filter the noisy measurements, such as the measurements received as signals from the plurality of IMU's 210 mounted on different portions and components of the machine 10, to estimate desired signals. The estimates derived by the Kalman filter from the signals provided by the IMU's and non-IMU sensors are statistically optimal in the sense that they minimize the mean-square estimation error of the signals. The state uncertainty estimate for the noisy measurements may be determined as a covariance matrix, where each diagonal term of the covariance matrix is the variance or uncertainty of a scalar random variable. A gain schedule module 222 may be configured to calculate weights (or gains) to be used when combining each successive predicted state estimate with a successive actual measurement value to obtain an updated "best" estimate. As the Kalman filter 240 receives multiple measurements over time from the IMU's 210 and the non-IMU sensors 230, a recursive algorithm of the Kalman filter processes each of the multiple measurements sequentially in time, iteratively repeating itself for each new measurement, and using only values stored from the previous cycle (thereby saving memory and reducing computational time).

In one exemplary embodiment, the memory 245 may include one or more pose estimation programs or subprograms loaded from storage 243 or elsewhere that, when executed by the processor 241, perform various procedures, operations, or processes consistent with disclosed embodiments. For example, the memory 245 may include one or more programs that enable the Kalman filter 240 to, among other things, collect data from the above-mentioned units and process the data according to disclosed embodiments such as those embodiments discussed with regard to FIG. 5, and determine a state of the machine 10 based on the processed data.

In certain embodiments, the memory 245 may store program enabling instructions that configure the Kalman filter 240 (more particularly, the processor 241) to implement a method that uses the Kalman filter to estimate a state of the machine 10. In certain exemplary embodiments, the Kalman filter may be configured to utilize the following equations in its calculations. For the propagation or "predict" phase, the Kalman filter may be configured to utilize the following generic equations:

$$\hat{x}_k^- = F_{k-1}\hat{x}_{k-1} + G_{k-1}u_{k-1} \quad (1)$$

$$P_k^- = F_{k-1}P_{k-1}^+ F_{k-1}^T + Q_{k-1} \quad (2)$$

For the measurement or "update" phase, the Kalman filter may be configured to utilize the following generic equations:

$$K_k = P_{k-1}^- H^T (H_k P_{k-1}^- H_k^T + R_k)^{-1} \quad (3)$$

$$\hat{x}_k^+ = \hat{x}_k^- + K_k(y_k - H_k\hat{x}_k^-) \quad (4)$$

$$P_k^+ = (I - K_k H_k) P_k^- \quad (5)$$

In the above equations, $\hat{x}_k^-$ may be the a priori state estimate of a certain state variable (e.g., pitch rate, yaw rate, roll rate, position, velocity, etc.) that is calculated based on a value ($\hat{x}_{k-1}$) of the state variable from an immediately preceding time step. F, G, and H may be appropriate state transition matrices. In the measurement or "update" phase, the Kalman filter 240 may calculate the Kalman gain $K_k$ utilizing equation (3), in which P is an error covariance matrix and R is a matrix setting forth the variance associated with the different state variables. For example, the values in the R matrix may specify the uncertainty associated with the measurement of a given state variable. In the measurement phase, the Kalman filter 240 may also obtain an independent measure of the state variable and set the independent measure as $y_k$. Utilizing the a priori estimate $\hat{x}_k^-$ from the "predict" phase, measurement $y_k$, and the Kalman gain $K_k$ (applied from the gain schedule module 222), the Kalman filter 240 may calculate the a posteriori state estimate $\hat{x}_k^+$ utilizing equation (4).

Figure 5:
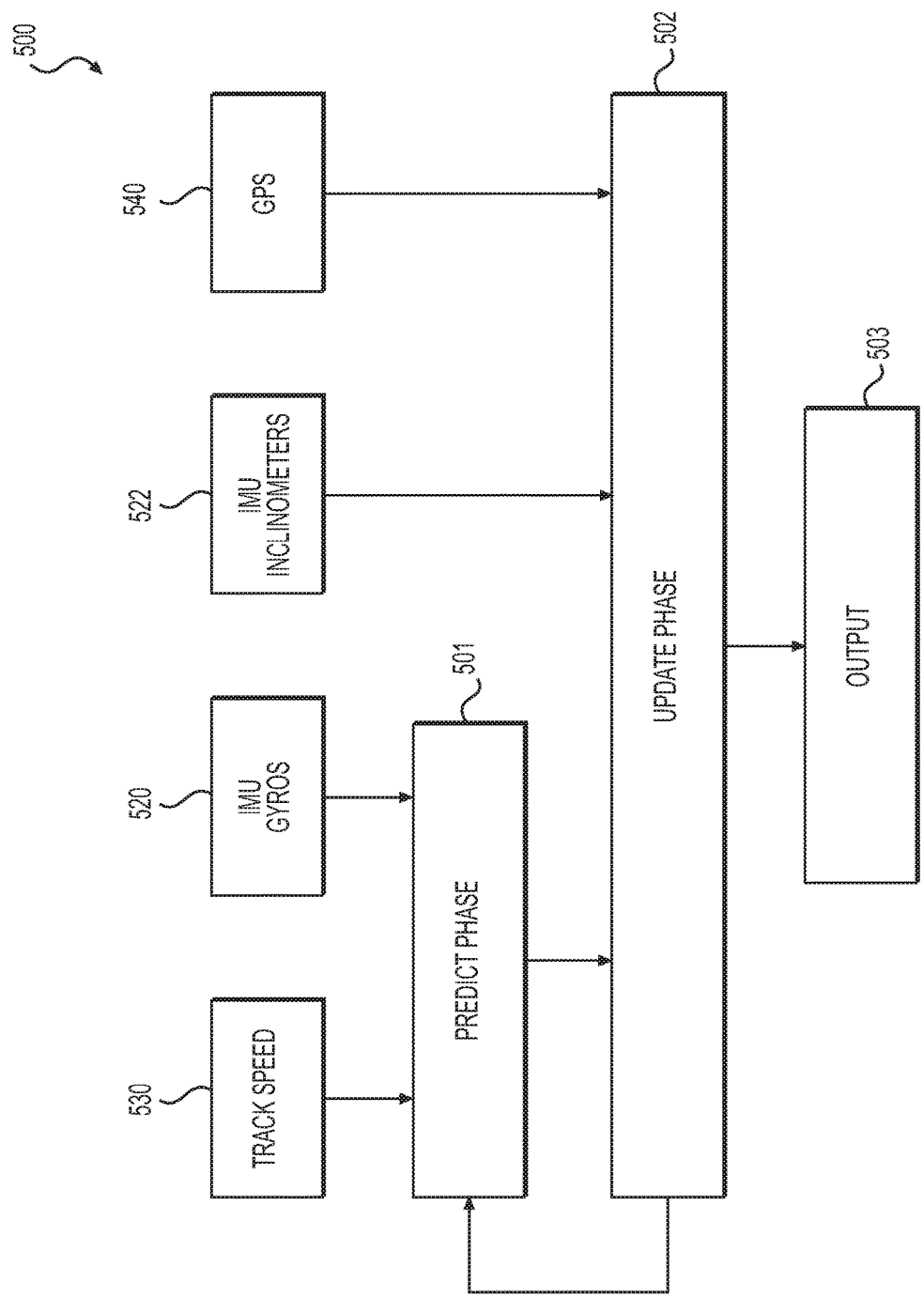
FIG. 5 is a diagrammatic illustration of an exemplary implementation of the sensor fusion system of FIG. 2.

FIG. 5 illustrates an exemplary configuration for a Kalman filter 500. In the predict phase 501 of the Kalman filter 500, the Kalman filter 500 may utilize one or more inputs from one or more IMU's (such as the linear acceleration values from an accelerometer of an IMU sensor and the angular rates of motion values from a gyroscope 520 of an IMU sensor) and a traction device speed sensor 530 to calculate an a priori state estimate of a certain state variable (e.g., pitch rate, yaw rate, roll rate, position, velocity, etc.) In the predict phase 501, the Kalman filter 500 may execute equations (1) and (2). For example, in the predict phase, the Kalman filter 500 may calculate $\hat{x}_k^-$ (a priori state estimate) of one or more state variables using a value ($\hat{x}_{k-1}$) of the state variable from an immediately preceding time step and the inputs from one or more IMU's 210 and/or a traction device speed sensor 530. In some exemplary implementations, $\hat{x}_{k-1}$ may be obtained from the update phase 502 as the output value of the immediately preceding time step.

Following the predict phase 501, the Kalman filter 500 may implement the update phase 502 to calculate the a posteriori state estimate $\hat{x}_k^+$ utilizing, for example, equation (4). For example, the Kalman filter 500 may calculate the a posteriori state estimate $\hat{x}_k^+$ using the a priori estimate $\hat{x}_k^-$ from the predict phase 501, measurement $y_k$, and the Kalman gain $K_k$ As shown in FIG. 5, the Kalman filter 500 may also receive as input, in the update phase 502, acceleration values from inclinometers 522 of the IMU's and location signals from one or more locating devices such as GPS devices 540 for machines that are visible to satellite.

The Kalman filter may set the input received from a locating device and from the inclinometers of the IMU's as the measurement $y_k$ in equation (4). Additionally, in an exemplary embodiment where the machine 10 is an excavator or other machine that includes portions or components that are rotated or swung through arcs during operation, the Kalman filter may receive acceleration values from the IMU's located on the rotating or swinging portion of the machine (e.g., the boom 17 and the stick 18) that have been pre-processed in a swing cancellation module 220 to compensate for centripetal acceleration occurring during the swinging motion. As shown in the exemplary embodiment of FIG. 2, the centripetal acceleration compensation for values from the IMU's 210 may be performed on the raw acceleration data from the IMU's 210 before the acceleration data is utilized in equation (4).

Also, as discussed above, the Kalman filter 500 in the exemplary embodiment of FIG. 5 may be configured to execute equations (3) and (5) in the update phase. Using the above, the Kalman filter may be configured to generate the a posteriori state estimate $\hat{x}_k^+$ as output 503. Without limitation, the a posteriori state estimate $\hat{x}_k^+$ may include the state of the machine, and may include parameters such as velocity, position, acceleration, orientation, etc.

The Kalman filter is very useful for combining data from several different indirect and noisy measurements to try to estimate variables that are not directly measurable. For example, the gyroscopes of the IMU's measure orientation by integrating angular rates, and therefore the output signals from the gyroscopes may drift over time. The inclinometer and direction heading features (compass) of the IMU's may provide a different noisy, but drift-free measurement of orientation. In the exemplary embodiment of FIG. 2, the Kalman filter may be configured to weight the two sources of information appropriately using weights retrieved from a gain schedule module 222 to make the best use of all the data from each of the sources of information.

In determining the state of the machine 10 using the Kalman filter 240, the filter may also be configured to consider other operational parameters of the machine 10. For example, if the machine 10 is an excavator, the Kalman filter may be configured to consider whether the machine 10 is digging, dumping, swinging in between digging and dumping positions, driving to a new location, etc. When the machine 10 is in one or more of the above operational states, certain parameters of the Kalman filter may be changed to reflect the accuracy or confidence in certain input parameters. For example, when the machine 10 is driving from one location to another, the Kalman filter may be configured to apply a lower weighting (gain) from the gain schedule module 222 to the input from the IMU inclinometers. To lower the weighting applied to the inclinometer input from the IMU's, the Kalman filter may be configured to increase the value of variance 'R' associated with the inclinometer input in equation (3). Similarly, when the machine 10 is digging, the Kalman filter may be configured to increase the weighting applied to the inclinometer input to reflect a higher confidence in the accuracy of the inclinometer input. For example, to indicate a higher confidence in the accuracy, the Kalman filter may be configured to apply a higher weighting (gain) from the gain schedule module 222 to the input from the IMU inclinometers and decrease the value of 'R' associated with the inclinometer input.

Figure 3:
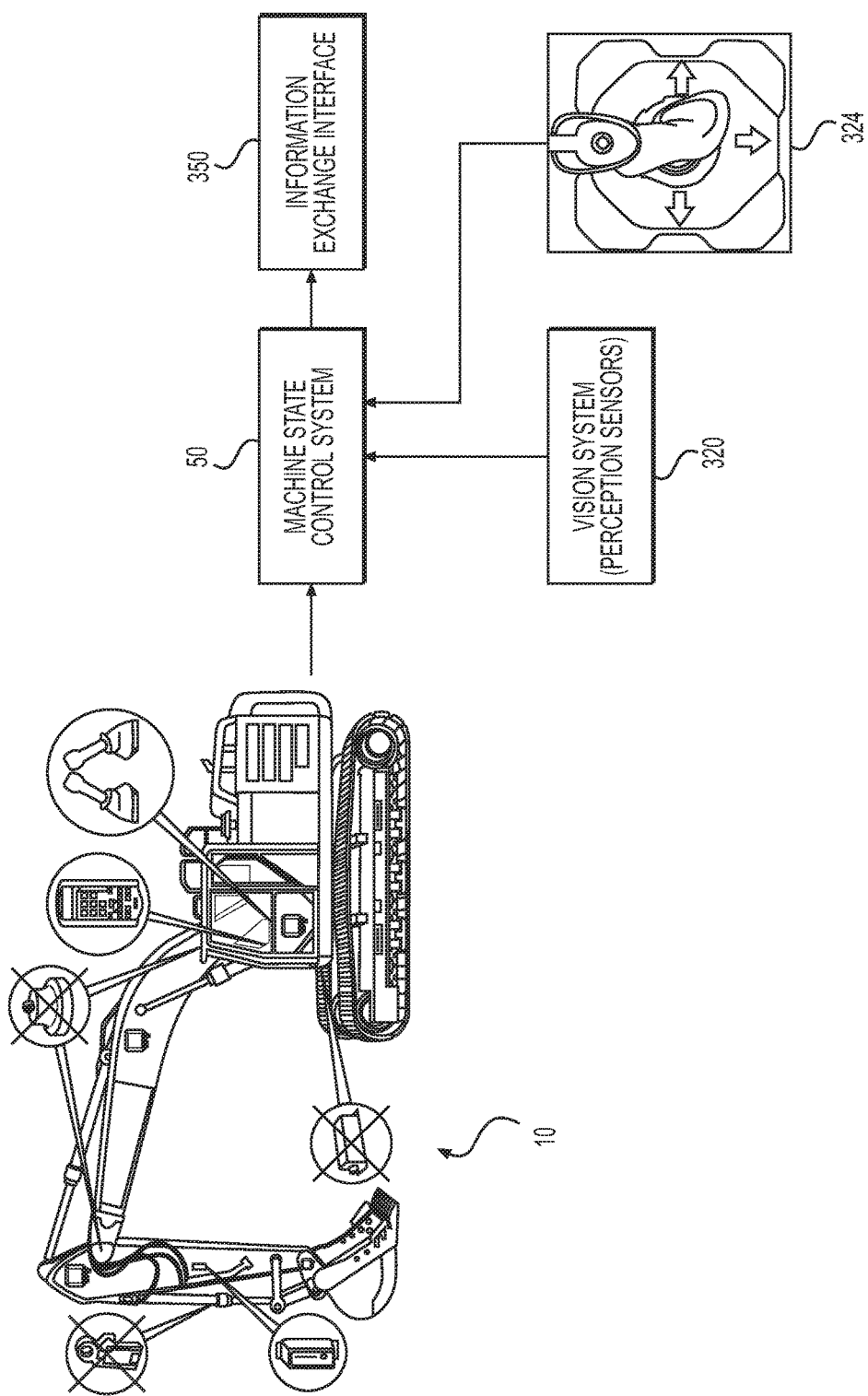
FIG. 3 is a diagrammatic illustration of an exemplary application of the outputs from the sensor fusion system of FIG. 2 for providing real time information used in controlling operations and pose of the exemplary disclosed machine of FIG. 1.
Figure 4:
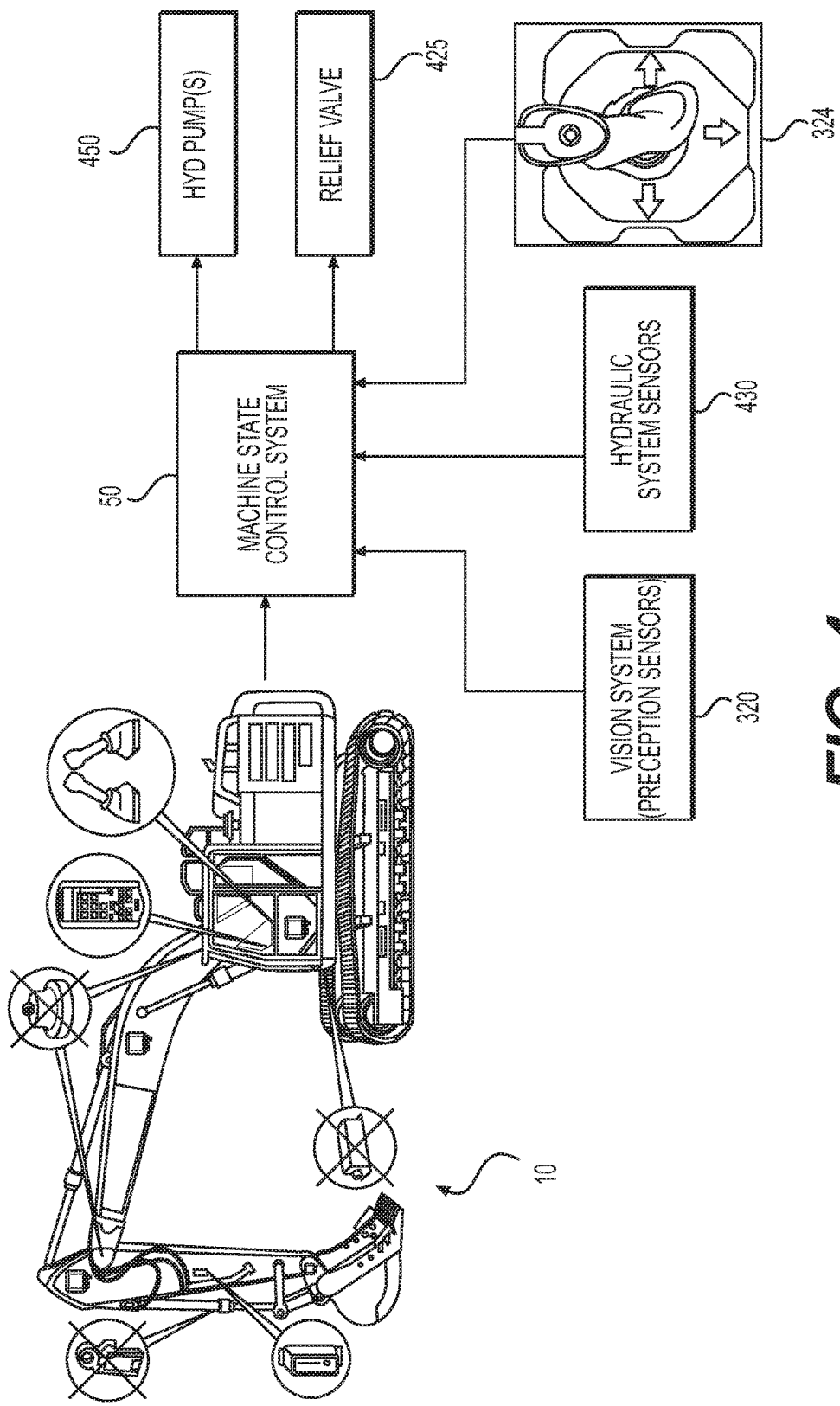
FIG. 4 is a diagrammatic illustration of an exemplary application of the outputs from the sensor fusion system of FIG. 2 for providing boosted hydraulic pressure outputs during selected operations of the exemplary disclosed machine of FIG. 1.

FIGS. 3 and 4 illustrate exemplary implementations of a machine state control system utilizing outputs from a sensor fusion system with a Kalman filter according to this disclosure. A detailed description of FIGS. 3 and 4 is provided in the next section.

INDUSTRIAL APPLICABILITY

The disclosed machine state control system 50 may be applicable to any machine or machine system benefiting from accurate, real time detection of the variables needed to completely describe the system behavior as a function of time (such as position, velocity, linear acceleration, and angular rate of motion of each machine component). The disclosed sensor fusion system in conjunction with multiple IMU's and non-IMU sensors retrofittably attached to different portions or components of the machine may provide for improved estimation of the positions and orientations of all of the different machine components by utilizing a Kalman filter associated with each IMU mounted on each of a plurality of machine components.

In some exemplary implementations of the disclosed sensor fusion system, the Kalman filter 240 may utilize machine parameters, odometer signals, and IMU inputs received from IMU's mounted on various portions and components of the machine to propagate or "predict" the machine states. For example, the Kalman filter 240 may predict the following states: position, forward velocity, angular velocities, joint angles, and angular orientation (attitude) of each of the machine components relative to global and machine reference frames, and of the machine itself relative to a global reference frame. In addition to the signals indicative of acceleration and angular rate of motion received from each IMU, each of the Kalman filters associated with each IMU mounted on a different machine component may receive, from a variety of different non-IMU sensors, such as an odometer, proximity sensors, and other perception sensors, signals indicative of the distance moved by the component of the machine during operation, or the distance between the component of the machine and a potential obstacle. The Kalman filter may also calculate the distance traveled by the machine 10 itself by multiplying a received scale factor by the number of rotations of a traction device. The Kalman filter may also calculate velocity of the machine 10 or velocity of a portion or component of the machine by integrating a signal indicative of linear acceleration from an IMU sensor mounted on a particular portion or component of the machine. The Kalman filter may calculate the velocity of the machine or the portion or component of the machine on which one or more IMU's are mounted using signals from the IMU's and weighting the resulting velocities to generate a predicted velocity. In some implementations, the distance traveled by the machine itself may be adjusted to account for slipping of the machine. Each Kalman filter may also receive signals indicative of the angular rates of motion (roll rate, yaw rate, and pitch rate) of the machine or portion of the machine from one or more IMU's. By integrating the angular rates of motion, the Kalman filter 240 may determine the attitude or angular orientation (roll, heading, and pitch) of each machine component or of the machine itself.

The Kalman filter may utilize one or more of the propagated states to propagate or "predict" the position of the machine 10 or the position of a portion or component of the machine relative to a machine reference frame and relative to a global reference frame. For example, by utilizing the angular rates of motion and predicted velocities, the Kalman filter may predict a position of the machine or component of the machine. As discussed above, the Kalman filter may also calculate an uncertainty for the predicted position that may be set equal to the uncertainty as designated by an error covariance matrix of the Kalman filter. Various positions on the machine may also be determined independently from the IMU's. Having determined the independent position measurements, the Kalman filter may be configured to fuse the predicted position information and the independent position measurement to determine updated position estimates for each location. Kalman filter measurement update equations may be utilized to determine the updated position estimate. Having determined an updated position estimate for the machine 10, the Kalman filter 240 may also determine the biases for each of the IMU's. As discussed above, an example of a bias parameter estimation that may be performed by the Kalman filter is an estimation of the bias of gyroscope determined angular positions after integration of measured angular rates.

In one exemplary application of the machine state control system according to an implementation of this disclosure, accurate, updated, real time information on the positions and orientations (pose) of the machine and portions or components of the machine may provide feedback to an information exchange interface 350 in order to effect machine controls that achieve optimal positioning and operation of the machine and components of the machine for improved productivity and reliability. In some implementations, the feedback may assist an operator by coaching the operator on how to effect controls that result in improved machine footing and stability, and hence improved productivity. In other implementations the information received at the information exchange interface 350 may result in the generation of autonomous or semi-autonomous control command signals that are provided to various machine systems and subsystems for effecting changes in machine pose and changes in the relative positions and orientations of machine components. In one exemplary implementation, as shown in FIG. 3, sensor feedback from machine sensors regarding machine linkage positions and velocity, machine pitch rate and roll rate, and swing angle for a boom and stick of an excavator may be fused with signals provided by a vision system and perception sensors 320 indicative of the locations of obstacles or other features at a job site, and signals received from various operator controls 324. The fused data may be provided to the information exchange interface 350 in order to effect the generation of control command signals that change the operation of various solenoid actuators, throttle controls, fluid cylinder actuation devices, electrical controls, and motion control devices to result in the optimal positioning of the machine during a digging operation. The information exchange interface 350 may provide accurate and real time updated information to a human operator in some implementations, as well as acting as an information interface with autonomous or semi-autonomous control systems that use the information to process control command signals for operating various machine systems and machine subsystems automatically or semi-automatically.

In digging with an excavator, the machine state control system 50 may determine from historical and/or empirical data regarding the kinematics and dynamics for the excavator that the car body of the machine should be parallel to the digging linkages with the idler wheels for the tracks of the excavator pointed toward the front linkages for the best stability during digging. Feedback can also be provided to the information exchange interface 350 regarding the machine pitch and roll so that if the footing is poor underneath the idler wheels when the tracks of the excavator are pointed forward, the information exchange interface can result in the generation of control command signals that cause a change in the pose of the machine to improve the footing and prevent the machine from pitching and rolling, as well as maneuvering the machine to make full contact with the ground to counteract digging forces. The angle of the bucket or other tool and the leverage being achieved by the particular orientation of the stick and boom at any particular point in time during a digging operation can also impact the digging efficiency of the excavator. The machine state control system according to this disclosure may provide continually updated feedback information to the information exchange interface regarding the real time efficiency of a linkage position during digging. The feedback information may result in a change to the angle of the bucket or the position of the stick during excavation in order to improve the efficiency of the machine by achieving better loading of the bucket, quicker loading of the bucket, and/or improved kinematics of the linkages that will result in a better use of the machine power and improve the longevity of the machine. The information provided to the information exchange interface from the machine state control system may also result in a change in control command signals that cause a change in the pose of the machine to avoid digging with the car body oriented at 90 degrees to the linkage, which is not optimal for stability or digging. When machine controls respond to the information provided at the information exchange interface 350 to implement controls such that the car body of the machine is parallel to the digging linkages with the idler wheels for the tracks of the excavator pointed toward the front linkages, the result is that energy is not wasted lifting the machine off the ground, productivity rates are increased with the resulting reduced cycle times, and loads on the final drive components are reduced for improved longevity of the machine and reduced down time.

In another exemplary application of the machine state control system according to this disclosure, as shown in FIG. 4, the sensor fusion system may receive, combine, and process operator command inputs received from operator controls 324 with inputs from IMU's and non-IMU machine sensors that measure linkage position, fluid pressures, engine speed, machine and machine component positions and orientations (including pitch rate, yaw rate, and roll rate), inputs from a vision system 320 that includes perception sensors providing signals indicative of the presence and location of objects, and inputs from hydraulic system sensors 430. In some implementations, the signal inputs from the hydraulic system sensors may be indicative of conditions under which higher pressures for fluid actuation cylinders are needed to avoid stalling. In order to avoid unnecessary stresses on the machine, components, and structures, the machine state control system 50 may be configured to automatically adjust boost pressures of hydraulic pumps 450 and command a controlled ramp up in relief pressure set points for one or more relief valves 425 if possible without causing damage to the machine or creating instabilities. The fused sensor outputs from the sensor fusion system according to various embodiments of this disclosure allow the machine state control system to determine when the machine may be stalling or about to stall during a lifting or digging operation. The machine state control system may then determine when and how much to boost relief pressure settings for the relief valve(s) 425 based on the fused sensor feedback information in combination with operator commands.

In one exemplary implementation, an excavator may be lifting a heavy load or performing a digging operation, and the boom actuation cylinder(s) may be at their maximum pressure, with the pump output pressure equal to the pressure in the boom actuation cylinders and the boom stalled while the bucket and stick are still moving. The machine state control system can determine from the accurate, real time fused sensor data being received from the sensor fusion system, including data indicative of the pitch rate, and roll rate for the machine, whether the machine is in an unstable and/or overstressed state. The machine state control system may determine that the relief pressure for the boom actuation cylinder(s) can be increased in a controlled ramp up to get the boom moving again without exceeding acceptable stress levels, and while maintaining the stability of the machine.

In additional exemplary implementations of the machine state control system according to this disclosure, the machine state control system may output commands to adjust the maximum output pressure of a pump providing pressurized fluid to various fluid actuation cylinders on the machine. As shown in FIG. 4, the machine state control system 50 receives the fused sensor data from the sensor fusion system, including operator inputs, measured linkage positions, fluid pressures, engine speeds, machine pitch rates and roll rates, and scene data such as the presence and location of objects. The machine state control system may determine what operations are being conducted, and adjust the maximum pressures allowed in the system electronically through high pressure cut offs that are established for different operations. The system can thereby prevent excessive stresses on various components and structures of the machine, and also prevent over-torqueing of the components or slamming of the components into objects at high rates of speed by slowing down pump flow, varying swing motor displacement, or overriding valve commands received from operator inputs. For components of a machine such as the boom and stick of an excavator, which may include an associated dedicated hydraulic swing circuit for moving the boom and stick between digging and dumping positions, the hydraulic pressure in the swing circuit or swing motor displacement can be electronically limited in accordance with real time output commands received from the machine state control system. In some implementations, one or more pumps provided in the swing circuit or other hydraulic circuits on the machine may be adaptable to a zero displacement or near-zero displacement operational configuration. The machine state control system 50 may determine what operations are being conducted, and adjust the displacement of the one or more pumps to a zero or near-zero displacement in certain situations. The displacement of the one or more pumps may be adjusted to a low enough value that only leakage of the system is compensated for, and movement of a linkage by a fluid actuation cylinder supplied by the pump or pumps in a very low displacement mode will not result in overstressing of the linkage or other machine components. In addition to or as an alternative to overriding valve commands or other control commands received from operator inputs in a semi-autonomous mode, the machine state control system 50 may provide feedback directly to an operator through one or more displays associated with the information exchange interface 350, or through haptic feedback in joysticks, the operator seat, heads-up displays (HUD) projected onto a windshield of the operator cab, or through sounds and other stimuli implemented to coach the operator and improve future operational control commands.

It will be apparent to those skilled in the art that various modifications and variations can be made to the disclosed method and system for determining the real time state of a machine. Other embodiments and implementations will be apparent to those skilled in the art from consideration of the specification and practice of the disclosed machine state control system. It is intended that the specification and examples be considered as exemplary only, with a true scope being indicated by the following claims and their equivalents.

What is claimed is:

1. A method of using sensor fusion feedback in the control of fluid pressures in a machine, comprising:
    receiving, with at least one processor, from each of a plurality of Inertial Measurement Units (IMU's) mounted on different components of the machine, a time series of signals indicative of acceleration and angular rate of motion measurements for each of the components of the machine on which one or more of the plurality of IMU's are mounted;
    receiving, with at least one processor, from at least one non-IMU sensor, a signal indicative of at least one of position, velocity, or acceleration of at least one of the machine components, position, velocity, or acceleration of any potential obstacles or other features at a job site where the machine is operating, a fluid pressure, an engine speed, a fluid relief pressure, a maximum pump output pressure, or an operator input;
    for each one of the IMU's on a separate component of the machine, fusing the signals received from the IMU with a separate Kalman filter module of the at least one processor, the fusing of the signals from each one of the plurality of IMU's comprising:
        combining an acceleration measurement and an angular rate of motion measurement from the IMU to estimate an output joint angle for the component of the machine on which the IMU is mounted during a timestep of a series of timesteps;
        generating an a priori estimate of the output joint angle for the component in a subsequent timestep based on an estimate of the output joint angle from a previous timestep;
        combining the a priori estimate of the output joint angle with an estimate of the accuracy of the a priori estimate and a current measurement value received from the IMU to produce a refined a posteriori estimate of the output joint angle;
    fusing the refined a posteriori estimates of the output joint angles for a plurality of the components of the machine with each other, with a signal from the at least one non-IMU sensor, and in reference to a machine reference frame to determine best estimates of current output joint angles for each of the plurality of components of the machine with reference to the machine reference frame;
    solving a kinematic equation using the best estimates of current output joint angles for the components of the machine and structural design information characterizing the machine;
    determining from the solution of the kinematic equation whether a higher fluid pressure to a fluid actuation cylinder connected between two of the machine components is required to avoid stalling of one of the two machine components relative to the other of the two machine components under load after each successive timestep of the series of timesteps;
    determining from the solution of the kinematic equation whether an adjustment to a pressure cut off for a fluid pump on the machine is required for an operation; and
    applying a determination from the solution of the kinematic equation in an implementation of a controlled adjustment to a fluid pressure supplied to the fluid actuation cylinder.

2. The method of claim 1, wherein the separate Kalman filter modules for each of the plurality of IMU's on the separate components of the machine perform an estimation of bias of measurements received from a gyroscope associated with each IMU, and compensate for the bias.

3. The method of claim 1, further including determining from successive positions of each machine component of interest whether a machine component is being moved in an arc during a swinging motion of the machine, and compensating for centripetal acceleration of a machine component that is being moved in an arc in acceleration measurements received from an IMU mounted on the machine component before inputting the acceleration measurements to a Kalman filter module.

4. The method of claim 1, further including determining the accuracy of an a posteriori estimate of an output joint angle based on an estimate of the accuracy of an actual measured value received from an IMU.

5. The method of claim 4, further including determining a weight to be associated with each successive a priori estimate of an output joint angle for a machine component relative to a weight to be associated with each successive a posteriori estimate based on successive actual measured values received from each IMU, and assigning a Kalman gain representative of the relative weights.

6. The method of claim 5, further including assigning the Kalman gain by retrieving from a predetermined gain schedule a state covariance matrix representative of the predicted variability in the a priori estimates of each output joint angle for a machine component, and an estimated measurements covariance matrix representative of the predicted variability in the actual measurements received from each IMU.

7. The method of claim 1, further including determining from the solution of the kinematic equation for each machine component whether to implement a controlled ramp up in a fluid relief pressure for fluid being supplied to the fluid actuation cylinder to avoid stalling of the machine component without causing any damage to the machine or creating any instabilities in the operation of the machine.

8. The method of claim 1, further including determining from the solution of the kinematic equation for each machine component whether to adjust a maximum fluid pressure allowed to the fluid actuation cylinder by one of increasing or decreasing a pressure cut off for a pump during a successive time step of an operation based on a best estimate of current output joint angles for the components of the machine and structural design information characterizing the machine.

9. The method of claim 1, further including:
receiving, with the at least one processor, a signal from a non-IMU sensor located on the machine, the signal from the non-IMU sensor being indicative of at least one of position, velocity, and acceleration of a machine component, and a fluid pressure being supplied to a fluid actuation cylinder operatively connected to the machine component; and
fusing the signal received from the non-IMU sensor with a signal received from an IMU mounted on a machine component using the separate Kalman filter module also used to fuse the signals received from the IMU.

10. A system for using sensor fusion feedback in the control of fluid pressures in a machine, comprising:
a plurality of Inertial Measurement Units (IMU's) mounted on separate components of the machine, the IMU's each being configured to generate a time series of signals indicative of acceleration and angular rate of motion measurements for the component of the machine on which the IMU is mounted;
at least one non-IMU sensor configured to generate a signal indicative of at least one of position, velocity, or acceleration of at least one of the machine components, position, velocity, or acceleration of any potential obstacles or other features at a job site where the machine is operating, a fluid pressure, an engine speed, a fluid relief pressure, a maximum pump output pressure, or an operator input; and
at least one processor in communication with each of the IMU's and the at least one non-IMU sensor, each of the at least one processor being configured to:
fuse the signals received from the IMU with a separate Kalman filter module of the at least one processor, the fusing of the signals from each one of the plurality of IMU's comprising:
combining an acceleration measurement and an angular rate of motion measurement from the IMU to estimate an output joint angle for the component of the machine on which the IMU is mounted during a timestep of a series of timesteps;
generating an a priori estimate of the output joint angle for the component in a subsequent timestep based on an estimate of the output joint angle from a previous timestep; and
combining the a priori estimate of the output joint angle with an estimate of the accuracy of the a priori estimate and a current measurement value received from the IMU to produce a refined a posteriori estimate of the output joint angle; and
fuse the refined a posteriori estimates of the output joint angles for a plurality of the components of the machine with each other, with a signal from the at least one non-IMU sensor, and in reference to a machine reference frame to determine best estimates of current output joint angles for each of the plurality of components of the machine with reference to the machine reference frame;
solve a kinematic equation using the best estimates of current output joint angles for the components of the machine and structural design information characterizing the machine;
determine from the solution of the kinematic equation whether a higher fluid pressure to a fluid actuation cylinder connected between two of the machine components is required to avoid stalling of one of the two machine components relative to the other of the two machine components under load after each successive timestep of the series of timesteps;
determine from the solution of the kinematic equation whether an adjustment to a pressure cut off for a fluid pump on the machine is required for an operation; and
apply a determination from the solution of the kinematic equation in an implementation of a controlled adjustment to a fluid pressure supplied to the fluid actuation cylinder.

11. The system of claim 10, wherein the separate Kalman filter modules for each of the plurality of IMU's on the separate components of the machine perform an estimation of bias of measurements received from a gyroscope associated with each IMU, and compensate for the bias.

12. The system of claim 10, wherein the at least one processor is further configured to determine from successive positions of each machine component of interest whether a machine component is being moved in an arc during a swinging motion of the machine, and compensate for centripetal acceleration of a machine component that is being moved in an arc in acceleration measurements received from an IMU mounted on the machine component before inputting the acceleration measurements to a Kalman filter module.

13. The system of claim 10, wherein the at least one processor is further configured to determine the accuracy of an a posteriori estimate of an output joint angle based on an estimate of the accuracy of an actual measured value received from an IMU.

14. The system of claim 13, wherein the at least one processor is further configured to determine a weight to be associated with each successive a priori estimate of an output joint angle for a machine component relative to a weight to be associated with each successive a posteriori estimate based on successive actual measured values received from each IMU, and assign a Kalman gain representative of the relative weights.

15. The system of claim 14, wherein the at least one processor is further configured to assign the Kalman gain by retrieving from a predetermined gain schedule a state covariance matrix representative of the predicted variability in the a priori estimates of each output joint angle for a machine component, and an estimated measurements covariance matrix representative of the predicted variability in the actual measurements received from each IMU.

16. The system of claim 10, wherein the at least one processor is further configured to determine from the solution of the kinematic equation for each machine component whether to implement a controlled ramp up in a fluid relief pressure for fluid being supplied to the fluid actuation cylinder to avoid stalling of the machine component without causing any damage to the machine or creating any instabilities in the operation of the machine.

17. The system of claim 10, wherein the at least one processor is further configured to determine from the solution of the kinematic equation for each machine component whether to adjust a maximum fluid pressure allowed to the fluid actuation cylinder by one of increasing or decreasing a pressure cut off for a pump during a successive time step of an operation based on a best estimate of current output joint angles for the components of the machine and structural design information characterizing the machine.

18. The system of claim 10, wherein the at least one processor is further configured to:
receive a signal from a non-IMU sensor located on the machine, the signal from the non-IMU sensor being indicative of at least one of position, velocity, and acceleration of a machine component, and a fluid pressure being supplied to a fluid actuation cylinder operatively connected to the machine component; and
fuse the signal received from the non-IMU sensor with a signal received from an IMU mounted on a machine component using the separate Kalman filter module also used to fuse the signals received from the IMU.

19. A non-transitory computer-readable storage device storing instructions for enabling a processor to execute a method of using sensor fusion feedback in the control of fluid pressures in a machine, the method comprising:
receiving, with the processor, from each of a plurality of Inertial Measurement Units (IMU's) mounted on different components of the machine, a time series of signals indicative of acceleration and angular rate of motion measurements for each of the components of the machine on which one or more of the plurality of IMU's are mounted;
receiving, with the processor, from at least one non-IMU sensor, a signal indicative of at least one of position, velocity, or acceleration of at least one of the machine components, position, velocity, or acceleration of any potential obstacles or other features at a job site where the machine is operating, a fluid pressure, an engine speed, a fluid relief pressure, a maximum pump output pressure, or an operator input;
for each one of the IMU's on a separate component of the machine, fusing the signals received from the IMU with a separate Kalman filter module of the processor, the fusing of the signals from each one of the plurality of IMU's comprising:
combining an acceleration measurement and an angular rate of motion measurement from the IMU to estimate an output joint angle for the component of the machine on which the IMU is mounted during a timestep of a series of timesteps;
generating an a priori estimate of the output joint angle for the component in a subsequent timestep based on an estimate of the output joint angle from a previous timestep;
combining the a priori estimate of the output joint angle with an estimate of the accuracy of the a priori estimate and a current measurement value received from the IMU to produce a refined a posteriori estimate of the output joint angle;
fusing the refined a posteriori estimates of the output joint angles for a plurality of the components of the machine with each other, with a signal from the at least one non-IMU sensor, and in reference to a machine reference frame to determine best estimates of current output joint angles for each of the plurality of components of the machine with reference to the machine reference frame;
solving a kinematic equation using the best estimates of current output joint angles for the components of the machine and structural design information characterizing the machine;
determining from the solution of the kinematic equation whether a higher fluid pressure to a fluid actuation cylinder connected between two of the machine components is required to avoid stalling of one of the two machine components relative to the other of the two machine components under load after each successive timestep of the series of timesteps;
determining from the solution of the kinematic equation whether an adjustment to a pressure cut off for a fluid pump on the machine is required for an operation; and
applying a determination from the solution of the kinematic equation in an implementation of a controlled adjustment to a fluid pressure supplied to the fluid actuation cylinder.

20. The non-transitory computer-readable storage device of claim 19, wherein the method further comprises:
performing an estimation of bias of measurements received from a gyroscope associated with each IMU by the Kalman filter module for the IMU on a component of the machine;
compensating for the bias in the gyroscope measurements with the processor;
determining from successive positions of each machine component of interest whether a machine component is being moved in an arc during a swinging motion of the machine; and
compensating for centripetal acceleration of a machine component that is being moved in an arc in acceleration measurements received from an IMU mounted on the machine component before inputting the acceleration measurements to the associated Kalman filter module.

* * * * *